United States Patent [19]

Sapatino

[11] Patent Number: 4,634,676
[45] Date of Patent: Jan. 6, 1987

[54] REPLICA PLATING DEVICE

[75] Inventor: Bruno V. Sapatino, Oxnard, Calif.

[73] Assignee: Becton, Dickinson and Company, Franklin Lakes, N.J.

[21] Appl. No.: 617,669

[22] Filed: Jun. 6, 1984

[51] Int. Cl.$^4$ ............................................... C12M 1/28
[52] U.S. Cl. .................... 435/294; 435/298; 435/299; 435/301
[58] Field of Search ............... 435/287, 292, 293, 294, 435/297, 298, 299, 300, 301

[56] References Cited

U.S. PATENT DOCUMENTS 2,348,448 5/1944 Brewer ................................. 435/298
3,203,870 8/1965 Andelin ................................ 435/298

FOREIGN PATENT DOCUMENTS 85839 1/1983 European Pat. Off. ............ 435/292

OTHER PUBLICATIONS

*Microbial World;* Stainer et al.; Prentice Hall, Inc. pp. 435–436.
*Microbiology;* Davis et al., Harper & Rowe; p. 175.

Primary Examiner—Alan Cohan
Attorney, Agent, or Firm—Richard J. Rodrick

[57] ABSTRACT

A replica plating device for use with an open-ended container which holds a plurality of cells on a culture medium therein comprises a substantially planar pressing member. A side wall extends upwardly from the pressing member and surrounds same. A skirt is connected to the side wall and extends downwardly from its connection point in the direction toward said pressing member along the exterior surface of said side wall in spaced relation thereto. As a result, the side wall and skirt form a hook for maintaining the device in position on the container to allow limited, controlled movement of the device for replica plating of cells within the container. A method of using a device substantially as described above for obtaining print-replicas of cells or the like is also within the purview of the present invention.

13 Claims, 6 Drawing Figures

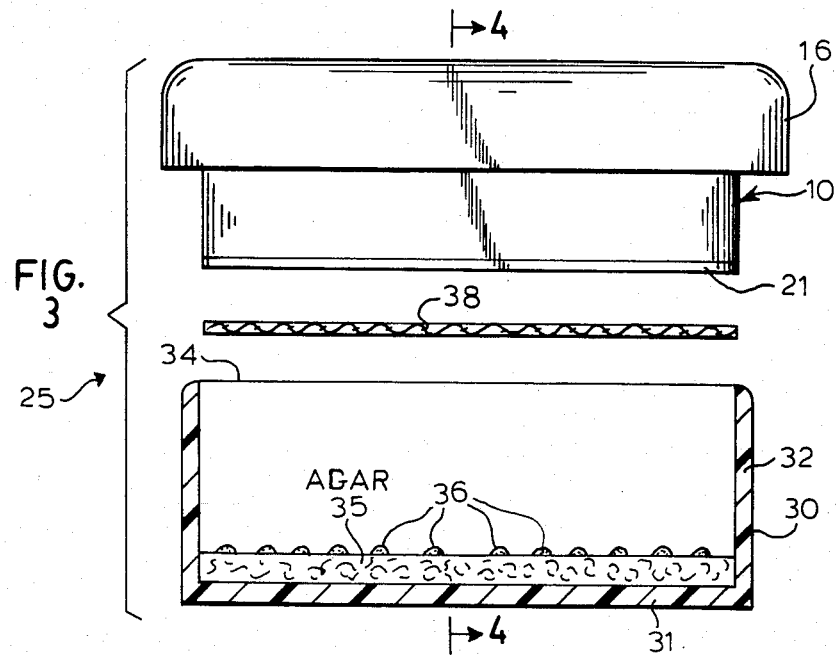
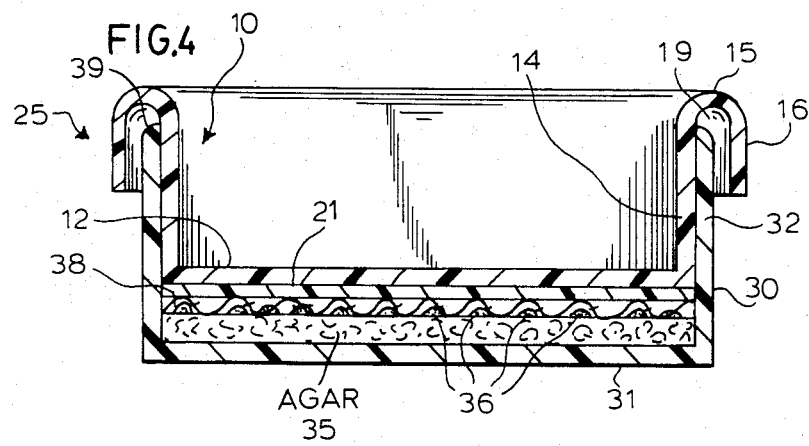

REPLICA PLATING DEVICE

BACKGROUND OF INVENTION

1. Field of the Invention.

The present invention relates to a replica plating device and its method of use, and more particularly, concerns such a device and its method for obtaining print-replicas of cells or the like from the surface of a culture medium within an open-ended container such as a petri dish.

2. Description of the Prior Art.

Laboratory investigations and research on cells are facilitated by the replication and subsequent identification of the cells of interest. It is often desirable to clone these cells which have certain characteristics in order to produce abundant quantities for the specific investigations relating to those cells. One technique for topographically duplicating colonies of cells and for conducting tests to duplicate select colonies is known as replica plating.

In the replica plating technique, an array of cell colonies is typically printed on a culture medium such as sterile agar medium. The array of cell colonies may consist of a pre-arranged pattern of spots printed on the agar surface, with sufficient clearance between each spot of cells to allow the diameter of the spot to grow as the number of cells therein replicate. Typically, the array may consist of 96, 108 or 144 spots of cells arranged in orthogonal rows and columns. For the replica plating transfer to occur, a replica filter, such as a Whatman filter paper, is placed over the colonies of cells and a replica plating tool is used to apply slight pressure against the filter paper. This pressure causes transfer of the array of cell colonies from the agar medium to the filter paper. Once the cell colonies have been print-plated onto the filter paper, the cell colonies can then be again replicated from this filter paper onto the surface of another agar medium or onto another filter. These transfers permit screening of the cell colonies to isolate those cells of interest. Since the replica plating provides for the transfer of colonies in the same pattern that the original colonies were incubated, ready identification of the source of cells of interest is the advantageous by-product of this technique.

Various replica plating procedures have been described in the following publications: Hirschberg, J. and Marcus, M., "Isolation by a Replica-Plating Technique of Chinese Hamster Temperature-Sensitive Cell Cycle Mutants," Journal of Cellular Physiology, 113:159–166 (1982); Klebe, R.J. et al., "Replica Plating of Cultured Mammalian Cells," Somatic Cell Genetics, Vol. 7, No. 3 pages 271–280 (1981); Gergen, J.P. et al., "Filter Replicas and Permanent Collections of Recombinant DNA Plasmids," Nucleic Acids Research, Vol. 7, No. 8, pages 2115–2136, (1979); and Suzuki, F. et al., "A Replica Plating Method of Cultured Mammalian Cells for Somatic Cell Genetics," Experimental Cell Research, Vol. 68, pages 476–479, (1971).

A typical replica plating tool, presently known and used, is disclosed in *Molecular Cloning* by T. Maniatis, published by Cold Spring Harbor Laboratory, 1982, page 306. This known and used replica plating tool resembles a hand-stamping instrument with a bottom pressure surface and an upwardly extending post for hand gripping. The bottom pressing surface includes a velvet layer to cushion the pressure of the filter paper against the cell colonies on the culture medium. To control the depth to which the known replica plating tool can penetrate into a petri dish, a horizontal depth stop is provided. Adjustment of this depth stop, due to its horizontal or lateral position, is awkwardly accomplished; further, there is some doubt that the known replica plating tool insures preservation of sterility in the petri dish from which the cell colonies are plate printed. Accordingly, there is a need to improve the characteristics of such a replica plating tool particularly for ease of use, the time required for use and degree of skilled involved, as well as improvements in sterility capabilities and disposability after a single use. One object of the present invention is the satisfaction of the needs perceived for such a replica plating tool.

SUMMARY OF THE INVENTION

The replica plating device of the present invention is for use with an open-ended container which holds a plurality of cells or the like on a culture medium. This device comprises a substantially planar pressing member and a side wall extending upwardly from the pressing member and surrounding same. A skirt is connected to the side and extends downwardly from its connection point in the direction toward the pressing member along the exterior surface of the side wall in spaced relation thereto. As a result, the side wall and skirt form a hook for maintaining the device in position on the container to allow limited, controlled movement of the device for replica plating of cells within the container.

In another aspect of the present invention, a replica plating assembly for obtaining print-replicas of cells or the like comprises a petri dish having a bottom surface and an annular rim extending upwardly from the bottom surface. A semi-solidified culture medium is on the bottom surface in the petri dish with colonies of cells in a random or pre-determined pattern on the top surface of the culture medium. Positioned over the cells and the top surface of the culture medium is a replica filter. Included in this assembly is a replica plating member having a pressing surface lying in substantially parallel juxtaposition with the top surface of the culture medium. An annular flange extends upwardly from the pressing surface and is positioned inwardly from the annular rim of the petri dish. An annular skirt extends from the flange over the rim and depends downwardly along the exterior surface of the rim. Movement of the pressing surface toward the culture medium presses the filter against the cells to thereby plate-print the cells onto the filter in the same arrangement, whether random or pre-determined pattern, which said cells appeared on the culture medium surface.

In a further aspect of the present invention, a method for obtaining print-replicas of cells or the like from the surface of a culture medium within an open-ended container having an upwardly extending rim comprises positioning a replica filter over the cells and the culture medium. A replica plating device is inserted into the container. This replica plating device is comprised of a substantially planar pressing member, a side wall extending upwardly from the pressing member and surrounding same, and a skirt connected to the side wall and extending downwardly along the side wall in spaced relation thereto. A hook is formed by the relationship of the side wall and the skirt. The method includes positioning the hook over the free end of the rim and pressing the plating device downwardly. This downward movement causes the pressing member to press the filter against the culture medium with controlled movement of the replica plating device. As a result, cells on the culture medium surface are plate-printed onto the filter in the same arrangement in which the cells appeared on the culture medium.

In accordance with the principles of the present invention, the replica plating device, assembly and its method for use all achieve the desired goals as set forth above and overcome the deficiencies in the known and used replica plating tool, also described above. Consistent with the achievement of the desired goals, the present invention can be inexpensively fabricated, and is amenable to injection molding techniques if the device is made out of polymeric material, which is the material of choice. As a result, the replica plating device of the present invention may be packaged in a sterilized condition so that it is ready for use. Furthermore, due to the inexpensive nature of the present device, it may be employed as a single-use item and, after such use, may be disposed instead of cleaning and sterilizing, which are labor-intensive techniques used on presently known devices. Of particular merit, the present replica plating device may be lowered directly onto the culture medium surface in a standard petri dish with no adjustment necessary to control the depth of penetration into the petri dish. Positioning of the present replica plating device into the standard petri dish is straightforward since the device acts and feels, to the user, like a lid. Due to the structure of the replica plating device which includes a skirt therearound that embraces and covers the rim of the petri dish containing the cells for cloning, preservation of sterility in the petri dish is more assured than use of the presently known and available replica plating tool. The present invention may further employ a soft or hard polymeric foam or brush on its pressing surface to provide a cushion effect when the device is pressed against the cells on the culture medium surface.

BRIEF DESCRIPTION OF THE DRAWINGS

FIG. 3 is an exploded, side elevational view of the elements of the preferred replica plating assembly of the present invention;

FIG. 4 is a cross-sectional view taken along line 4—4 of FIG. 3 with the elements of the replica plating assembly as they would appear assembled during the print-plating procedure;

DETAILED DESCRIPTION

Figure 1:
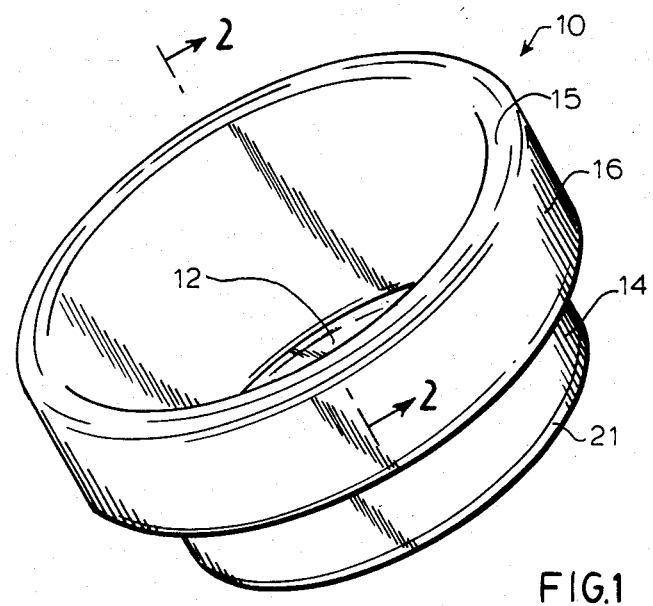
FIG. 1 is a perspective view of the preferred embodiment of the replica plating device of the present invention.

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

Figure 2:
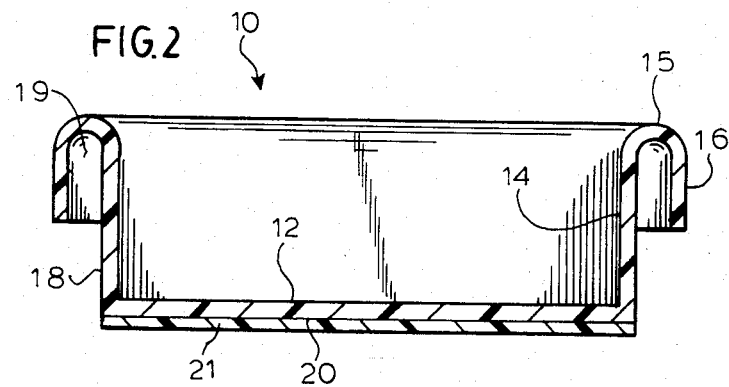
FIG. 2 is a cross-sectional view taken along line 2—2 of FIG. 1.

Adverting now to the drawings, and FIGS. 1 and 2 in particular, there is illustrated a replica plating device 10 for use in obtaining print-replicas of cells or the like. Device 10 is preferably a cylindrically shaped body having a substantially planar bottom wall 12. As will be described later, this bottom wall serves as a pressing member. Extending upwardly from bottom wall 12 is a side wall 14 which, in the embodiment illustrated is substantially cylindrically shaped and surrounds bottom surface 12. In this fashion, device 10 takes on the shape of a cup or lid as illustrated in the drawings. Cylindrical side wall 14, as it extends upwardly toward its free end, bends outwardly. While this outward bend is preferably a smooth, curving transition, it could be more squared-off than illustrated if desired during the formation of this device. Extending downwardly from free end 15 of the side wall is a skirt 16, which is preferably a continuation of the rolled-over section of the side wall. Skirt 16 extends downwardly along the exterior surface 18 of the side wall leaving an annular space 19 between the skirt and the side wall as the skirt points downwardly toward bottom surface 12. It can be seen that the skirt and the side wall together form a hook-like structure, the function of which shall be discussed below.

It is preferred that side wall 14 and skirt 16 be integrally formed as a unitary structure; such one-piece structure would facilitate the smooth bend between side wall and skirt and permit substantial concentricity between skirt and side wall. More preferably, the entire replica plating device is integrally formed as a unitary structure. Since the preferable materials out of which the plating device may be made include rigid polymeric materials, such as polystyrene, polypropylene and the like, injection molding may be employed to fabricate the device as a one-piece unit on an inexpensive basis.

Attached to the exterior surface 20 of the bottom wall is a layer of compressible material 21. This layer is preferably relatively thin, may be, for example, velvet, soft expanded polyurethane or hard polyurethane foam. It serves to cushion the pressing effect of the replica plating device against the cells and culture medium during use. The layer of compressible material 21 may be adhesively attached to exterior surface of the bottom wall of the replica plating device, but, of course, other attachment means may be utilized where feasible.

Referring now to FIGS. 3 and 4, a replica plating assembly 25 is illustrated employing replica plating device 10 as described above. FIG. 3 illustrates the replica plating device as it may be used with a standard petri dish 30 during the procedure for replica plating of cells. Petri dish 30 typically has a substantially flat bottom surface 31 and an annular rim 32 extending upwardly from the bottom surface thereby forming a substantially cylindrically shaped, open-ended cup. Into the open end 34 of the petri dish is typically deposited a small amount of a culture medium 35, such as agar, which is hardenable so that is solidifies to form a substantially semi-solid, but usually somewhat compressible, surface. As seen in FIG. 3, the agar medium normally occupies a thin layer on the bottom surface of the petri dish.

Colonies of cells 36 have been deposited on the top surface of the agar medium. Various means may be used to place these cells onto the agar surface, such as those procedures described in the above-mentioned literature publications. Typically, colonies of cells are placed on the agar surface in a pre-determined pattern of spots (containing cells) in rows and columns, although a random pattern may also be used. This allows the investigator to identify and keep track of the plurality of colonies on the agar surface. Sufficient space may be provided between each spot so that, following incubation, when the cells in the respective colonies replicate, the spot grows larger. As long as the enlargened colony spots do not merge, their separate identity may be maintained.

In order to screen and conduct further tests on these cell colonies, the replica plating technique includes the positioning of a replica filter 38 over the cells on the agar surface. Such replica filter may be Whatman filter paper as described in the aforementioned literature publications. Once the replica filter has been placed over the cells in the petri dish, replica plating device 10 is then inserted into the petri dish, as more clearly illustrated in FIG. 4.

Figure 5:
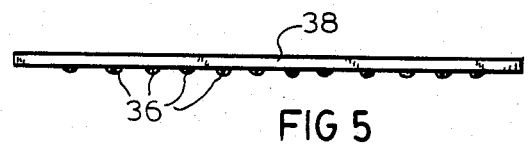
FIG. 5 is a side elevational view of the replica filter illustrating in schematic fashion the transfer of cells thereto subsequent to the pressing technique shown in FIG. 4.
Figure 6:
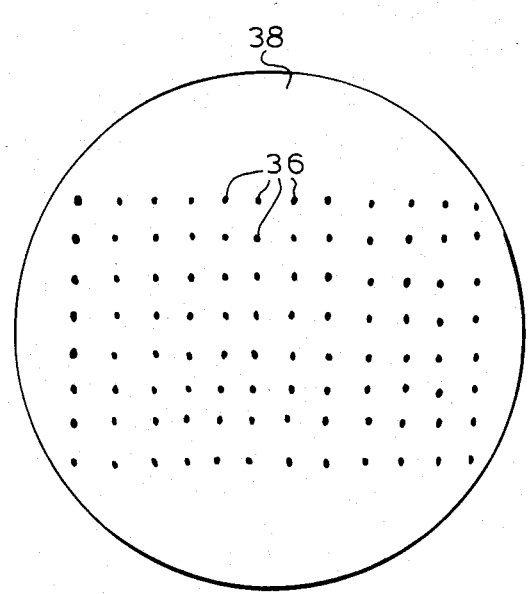
FIG. 6 is a bottom plan view of the replica filter of FIG. 5.

It can be seen that the annular flange or side wall 14 of the replica plating device slidably fits within upwardly extending rim 32 of the petri dish. The hook formed by side wall 14 and skirt 16 is positioned over free end 39 of rim 32. Once the hook is in position, it serves as a guide for controllably pressing the plating device into the petri dish. Thus, with replica filter 38 in position, downward movement of the plating device causes bottom wall 12 to exert a downward force across the top surface of the agar medium. This force is communicated through layer of compressible material 21 and replica filter 38. As a result, cells 36 are print-plated onto the filter in the same arrangement in which the cells appeared on the top surface of the agar medium. FIGS. 5 and 6 illustrate replica filter 38 after cells 36 have been print-plated thereon by virtue of the procedure seen in FIG. 4. With the cells now on the replica filter, further screening may be conducted on the various cell colonies to isolate those cells of interest. Further, the procedure illustrated in FIG. 4 may be reversed; i.e., cells which have been replica plated onto the replica filter may then be transferred to a different petri dish with a clean agar surface for further culturing. By the replica plating procedures described hereinabove, the investigator is able to trace the cells of interest to the original position the cell colony was deposited on the first agar surface. These cells may be isolated and then cloned, if desirable.

Inasmuch as the replica plating device described herein automatically lowers itself onto the agar surface, no adjustment is necessary to control the depth to which the plating device penetrates into the petri dish. Depth of penetration and controlled movement is afforded by the dimensions of the respective elements of the replica plating device. Specifically, the diameter of bottom wall 12 and outside surface 18 of side wall 14 is normally sized to allow the plating device to freely slide into a specific size, standard petri dish. Similarly, the diameter of the inside surface of skirt 16 is controlled so that it is slightly larger than the outside diameter of the rim of the petri dish. These aforementioned diameters then provide controlled movement of the replica plating tool into the petri dish. Depth penetration can be controlled by the height of side wall 14 with respect to the height of rim 32 of the petri dish, also taking into account the typical thickness of agar medium to be deposited in the petri dish, the thickness of the layer of compressible material 21 and the thickness of replica filter 38. While the length of skirt 16 should not exceed the length (or height) of side wall 14, it is preferred to keep the length of the skirt relatively short with respect to the side wall.

The replica plating device of the present invention is readily sterilizable using standard sterilizing techniques, and is preferably intended to be a single use item which is disposed after being used.

Thus, the present invention provides a replica plating device and a method of its use for obtaining print-replicas of cells from an open-ended container, such as a standard petri dish. Controlled movement of the device allows the plate printing of cells onto a replica filter in substantially the same arrangement which the cells appeared on the original culture medium surface. The configuration of the replica plating device hereof contributes to maintaining the sterility of the petri dish from which the cells have been obtained. Further, the replica plating device of the present invention may be packaged sterilized, and disposed after a single use.

What is claimed is:

1. A replica plating assembly for obtaining print-replicas of cells or the like comprising:
   a petri dish having a bottom surface and an annular rim extending upwardly from said bottom surface;
   a semi-solidified culture medium on the bottom surface in said petri dish with colonies of cells arranged on the top surface of said culture medium;
   a replica filter positioned over said cells and the top surface of said culture medium; and
   a replica plating device including a pressing surface lying in substantially parallel juxtaposition with the top surface of said culture medium, an annular flange extending upwardly from said pressing surface and positioned inwardly from the annular rim of said petri dish, and an annular skirt extending from said flange over said rim and depending downwardly along the exterior surface of said rim; whereby movement of said pressing surface toward said culture medium presses said filter against said cells to thereby plate-print said cells onto said filter in the same arrangement which said cells appeared on said culture medium surface.

2. A replica plating device for use with an open-ended container which holds a plurality of cells on a culture medium therein comprising:
   a substantially planar pressing member;
   a layer of compressible material overlying the exterior surface of said pressing member;
   a replica filter overlying said layer of compressible material;
   a side wall extending upwardly from said pressing member and surrounding same; and
   a skirt connected to the side wall and extending downwardly from its connection point in the direction toward said pressing member along the exterior surface of said side wall in spaced relation thereto so that said side wall and skirt form a hook for maintaining said device in position on said container to allow limited, controlled movement of the device for replica plating of cells within said container.

3. The device of claim 2 wherein said pressing member has a substantially circularly-shaped periphery.

4. The device of claim 3 wherein said side wall is in the shape of a substantially cylindrical annular flange around said pressing member.

5. The device of claim 4 wherein said skirt is connected to the free end of said flange.

6. The device of claim 4 wherein said skirt is substantially cylindrically shaped and is substantially concentrically spaced from said flange.

7. The device of claim 2 wherein said skirt extends along said side wall in substantially parallel arrangement thereto.

8. The device of claim 2 wherein said skirt is shorter in height than the height of said side wall.

9. The device of claim 2 wherein said side wall and said skirt are integrally formed as a unitary structure.

10. The device of claim 2 wherein said compressible material is a polymeric foam.

11. The device of claim 2 wherein said side wall and said skirt are made from rigid polymeric material.

12. The device of claim 11 wherein said material is polystyrene.

13. The device of claim 11 which is sterilized.

* * * * *